(12) United States Patent
Kárpáti et al.

(10) Patent No.: US 10,080,762 B2
(45) Date of Patent: Sep. 25, 2018

(54) PHARMACEUTICAL COMPOSITION CONTAINING CELECOXIB

(71) Applicant: Druggability Technologies IP Holdco Limited, Msida (MT)

(72) Inventors: Richárd Balázs Kárpáti, Tatabánya (HU); Nikoletta Erdősi, Nyiregyhaza (HU); Gergo Patyi, Vecsés (HU); Hristos Glavinas, Szeged (HU); Genovéva Filipcsei, Budapest (HU)

(73) Assignee: Druggability Technologies IP Holdco Limited, Msida (MT)

( * ) Notice: Subject to any disclaimer, the term of this patent is extended or adjusted under 35 U.S.C. 154(b) by 0 days.

(21) Appl. No.: 15/840,204

(22) Filed: Dec. 13, 2017

(65) Prior Publication Data

US 2018/0185393 A1    Jul. 5, 2018

Related U.S. Application Data

(60) Provisional application No. 62/434,173, filed on Dec. 14, 2016, provisional application No. 62/502,170, filed on May 5, 2017.

(51) Int. Cl.

| A61K 31/635 | (2006.01) |
|---|---|
| A61K 31/415 | (2006.01) |
| A61K 47/32 | (2006.01) |
| A61K 47/38 | (2006.01) |
| A61P 29/00 | (2006.01) |
| A61P 43/00 | (2006.01) |
| C07D 231/12 | (2006.01) |

(Continued)

(52) U.S. Cl.
CPC .......... *A61K 31/635* (2013.01); *A61K 9/0053* (2013.01); *A61K 9/146* (2013.01); *A61K 9/16* (2013.01); *A61K 31/095* (2013.01); *A61K 31/415* (2013.01); *A61K 31/79* (2013.01); *A61P 19/02* (2018.01); *A61P 29/00* (2018.01); *A61K 2300/00* (2013.01)

(58) Field of Classification Search
CPC ...... A61K 31/635; A61K 47/32; A61K 47/38; A61K 9/0053; A61K 9/146; A61K 9/16; A61K 31/095; A61K 31/415; A61K 31/79; A61P 19/02; A61P 29/00; C07D 231/12

See application file for complete search history.

(56) References Cited

U.S. PATENT DOCUMENTS

| 6,964,978 B2 | 11/2005 | Hageman |
|---|---|---|
| 7,220,434 B2 | 5/2007 | Desai |

(Continued)

FOREIGN PATENT DOCUMENTS

WO    2017103677    6/2017

OTHER PUBLICATIONS

United States Patent and Trademark Office, International Search Report and Written Opinion of the International Searching Authpority, dated Feb. 12, 2018 for PCT/US17/65997.

*Primary Examiner* — Savitha M Rao
(74) *Attorney, Agent, or Firm* — Dennis A. Bennett (57) ABSTRACT

Disclosed herein is a pharmaceutical composition comprising pharmaceutical formulation of complexed Celecoxib and crystalline Celecoxib to provide fast and long lasting continuous pain management with once a daily dosing. The pharmaceutical composition has improved physicochemical properties that provide faster onset of action for acute pain relief and lower GI related side effects for acute pain relief and lower GI related side effects.

14 Claims, 5 Drawing Sheets

(51) Int. Cl.
*A61K 31/79* (2006.01)
*A61K 31/095* (2006.01)
*A61K 9/14* (2006.01)
*A61K 9/16* (2006.01)
*A61P 19/02* (2006.01)
*A61K 9/00* (2006.01)

(56) References Cited

U.S. PATENT DOCUMENTS 8,846,744 B2    9/2014    Soler Ranzani
2016/0228455 A1    8/2016    Angi

|  | Papp (x10⁻⁶ cm/s) | | |
|---|---|---|---|
|  | H₂O | FASSIF | FESSIF |
| Micronised Celecoxib | 0.1885 | 0.0732 | 0.1298 |
| Celebrex® 200 mg | 0.1706 | 0.1043 | 0.1897 |
| Complexed Celecoxib formulation (API:Copovidone:SLS = 1:4:1 w/w) | 2.1227 | 1.6995 | 2.6325 |
| Complexed Celecoxib formulation (API:Copovidone:SLS = 1:4:0.5 w/w) | 3.2315 | 2.5184 | 2.4596 |
| Complexed Celecoxib formulation (API:Copovidone:SLS = 1:4:0.25 w/w) | 2.9444 | 2.2804 | 2.7026 |
| Complexed Celecoxib formulation (API:Copovidone:SLS = 1:3:0.25 w/w) | 4.0373 | 2.2990 | 3.3093 |
| Complexed Celecoxib formulation (API:Copovidone:SLS = 1:2:0.25 w/w) | 2.5030 | 2.6910 | 3.2487 |
| Celecoxib composition (Complexed formulation : micronized API = 1:2 w/w) | 0.7440 | 0.5940 | 0.7990 |

FIG. 4

|  |  | Papp (x10⁻⁶ cm/s) | | |
|---|---|---|---|---|
|  |  | H₂O | FASSIF | FESSIF |
| Celecoxib pharmaceutical composition* | t=0 | 0.7440 | 0.5940 | 0.7990 |
|  | t= 12 months storage at 40° | 0.7719 | 0.7276 | 0.8223 |
|  | t= 12 months storage at 40°C | 2.7726 | 2.3268 | 3.1830 |
| Complexed Celecoxib formulation | t= 3 months storage at 40°C** | 4.4366 | 3.1883 | 3.0999 |
|  | t= 3 months storage at 40°C*** | 3.1396 | 3.0645 | 3.4526 |

\* API content of complexed formulation : micronized API = 1:2 w/w
\*\* API:Copovidone:SLS = 1:4:0.5 w/w
\*\*\* API:Copovidone:SLS = 1:4:0.25 w/w

FIG. 5

PHARMACEUTICAL COMPOSITION CONTAINING CELECOXIB

This application claims priority to U.S. provisional application No. 62/434,173, filed Dec. 14, 2016 and U.S. provisional application No. 62/502,170, filed May 5, 2017, the disclosures of which are hereby incorporated by reference as if written herein in their entireties.

FIELD OF THE INVENTION

Disclosed herein are pharmaceutical compositions comprising a mixture of a pharmaceutical formulation of complexed Celecoxib and crystalline, uncomplexed Celecoxib to provide fast and long lasting continuous pain management with once daily dosing. The pharmaceutical compositions are useful in the treatment of osteoarthritis, rheumatoid arthritis, juvenile rheumatoid arthritis, ankylosing spondylitis, acute pain, primary dysmenorrhea. Further disclosed are methods of manufacturing the pharmaceutical compositions.

BACKGROUND OF THE INVENTION

The chemical name of Celecoxib is 4-[5-(4-methylphenyl)-3-(trifluoromethyl)-1H-pyrazol-1-yl] benzenesulfonamide and is a diaryl-substituted pyrazole. The molecular formula is $C_{17}H_{14}F_3N_3O_2S$, and the molecular weight is 381.38; the chemical structure is as follows:

Celecoxib is a white powder, insoluble in water, soluble in methanol and chloroform.

CELEBREX oral capsules contain either 50 mg, 100 mg, 200 mg or 400 mg of Celecoxib, together with inactive ingredients including: croscarmellose sodium, edible inks, gelatin, lactose monohydrate, magnesium stearate, povidone and sodium lauryl sulfate.

CELEBREX is a nonsteroidal anti-inflammatory drug that exhibits anti-inflammatory, analgesic, and antipyretic activities in animal models. The mechanism of action of CELEBREX is believed to be due to inhibition of prostaglandin synthesis, primarily via inhibition of cyclooxygenase-2 (COX-2), and at therapeutic concentrations in humans, CELEBREX does not inhibit the cyclooxygenase-1 (COX-1) isoenzyme. In animal colon tumor models, CELEBREX reduced the incidence and multiplicity of tumors.

Peak plasma levels of Celecoxib occur approximately 3 hrs after an oral dose. Under fasting conditions, both peak plasma levels ($C_{max}$) and area under the curve (AUC) are roughly dose-proportional up to 200 mg BID; at higher doses there are less than proportional increases in $C_{max}$ and AUC. Absolute bioavailability studies have not been conducted. With multiple dosing, steady-state conditions are reached on or before Day 5.

When CELEBREX capsules were taken with a high fat meal, peak plasma levels were delayed for about 1 to 2 hours with an increase in total absorption (AUC) of 10% to 20%. Under fasting conditions, at doses above 200 mg, there is less than a proportional increase in $C_{max}$ and AUC, which is thought to be due to the low solubility of the drug in aqueous media.

Co-administration of CELEBREX with an aluminum- and magnesium-containing antacids resulted in a reduction in plasma celecoxib concentrations with a decrease of 37% in $C_{max}$ and 10% in AUC. CELEBREX, at doses up to 200 mg twice daily, can be administered without regard to timing of meals. Higher doses (400 mg twice daily) should be administered with food to improve absorption.

In healthy adult volunteers, the overall systemic exposure (AUC) of Celecoxib was equivalent when Celecoxib was administered as intact capsule or capsule contents sprinkled on applesauce. There were no significant alterations in $C_{max}$, $t_{max}$, or $t_{1/2}$ after administration of capsule contents on applesauce.

In healthy subjects, Celecoxib is highly protein bound (~97%) within the clinical dose range. In-vitro, studies indicate that Celecoxib binds primarily to albumin and, to a lesser extent, α1-acid glycoprotein. The apparent volume of distribution at steady state (Vss/F) is approximately 400 L, suggesting extensive distribution into the tissues. Celecoxib is not preferentially bound to red blood cells.

Celecoxib metabolism is primarily mediated via CYP2C9. Three metabolites, a primary alcohol, the corresponding carboxylic acid and its glucuronide conjugate, have been identified in human plasma. These metabolites are inactive as COX-1 or COX-2 inhibitors.

Celecoxib is eliminated predominantly by hepatic metabolism with little (<3%) unchanged drug recovered in the urine and feces. Following a single oral dose of radiolabeled drug, approximately 57% of the dose was excreted in the feces and 27% was excreted into the urine. The primary metabolite in both urine and feces was the carboxylic acid metabolite (73% of dose) with low amounts of the glucuronide also appearing in the urine. It appears that the low solubility of the drug prolongs the absorption process making terminal half-life (t½) determinations more variable. The effective half-life is approximately 11 hours under fasted conditions. The apparent plasma clearance (CL/F) is about 500 mL/min.

The main medical concerns surrounding Celecoxib are related to slow absorption and variable first-pass metabolism of Celecoxib limit its utility for treatment of acute pain. When a single dose of 200 mg of current formulation is given, peak plasma levels occur 3 hours after an oral dose, however, onset of pain relief could be as early as 1 hour. When taken with a high fat meal, peak plasma levels are delayed for about 1 to 2 hours with an increase in total absorption (AUC) of 10% to 20%. Since it is a painkiller shortening this time and the elimination of the delay of peak plasma concentrations could be advantageous.

In order to overcome the problems associated with prior conventional Celecoxib formulations and available drug delivery systems, novel pharmaceutical compositions of Celecoxib comprising the pharmaceutical formulation of complexed Celecoxib and crystalline Celecoxib were prepared. The pharmaceutical formulation ensures the immediate absorption of Celecoxib via the complexed formulation, resulting in fast pain relief, while the crystalline component is responsible for delayed absorption and extended analgesic effect.

A variety of strategies have been used to attempt to overcome these issues, see for example US 20130338131, WO 2009114695, U.S. Pat. No. 7,879,360, US 20090098200, WO 2003080027, US 20150011514, U.S. Pat. No. 6,964,978, U.S. Pat. No. 7,220,867, WO 2001042221, WO 2001095877, WO 2001091750, WO 2014018932, WO 2004078163, WO 2004047752, WO 2007010559, WO 2013132457 and WO 2001041760.

DESCRIPTION OF THE INVENTION

Disclosed herein are pharmaceutical compositions comprising the mixture of a complexed pharmaceutical formulation of Celecoxib and crystalline Celecoxib; said pharmaceutical compositions are characterized in that they possess at least one of the following properties:
a) is instantaneously redispersable in physiological relevant media;
b) has an apparent solubility in water of at least 1 mg/mL;
c) has biphasic dissolution profile: complexed pharmaceutical formulation of Celecoxib dissolves from the composition within 45 minutes, while crystalline Celecoxib has continuous dissolution;
d) has a PAMPA permeability of at least $0.5 \times 10^{-6}$ cm/s when dispersed in fasted state simulated intestinal fluid (FaSSIF) or fasted state simulated intestinal fluid (FeSSIF) biorelevant media; which does not decrease in time at least for 3 months stored at 40° C.
e) has a blood plasma level that reaches 250 ng/ml Celecoxib in less than 60 minutes when administered orally.

In an embodiment, said composition further comprises a pharmaceutically acceptable excipient.

In an embodiment, said complexed pharmaceutical formulation of Celecoxib dissolves from the composition within 30 minutes.

In an embodiment, said complexed pharmaceutical formulation of Celecoxib dissolves from the composition within 15 minutes.

In an embodiment, said blood plasma level is reached in less than 45 minutes.

In an embodiment, said blood plasma level is reached in less than 30 minutes.

In an embodiment, said blood plasma level is reached in less than 20 minutes.

In an embodiment, said blood plasma level is reached in less than 15 minutes.

In an embodiment, said plasma concentration is maintained for at least 12 hours.

The complexed pharmaceutical formulation comprising complexed Celecoxib ensures the immediate absorption of Celecoxib resulting in fast pain relief, while the crystalline component is responsible for delayed absorption and extended analgesic effect.

It has been found that only the combination of pharmaceutical formulation of complexed Celecoxib and crystalline Celecoxib resulted in a pharmaceutical composition which delivers early therapeutic blood plasma levels which is at least 250 ng/mL to ensure the fast pain relief and sustained Celecoxib dissolution to maintain the therapeutic blood plasma level for at least 12 h after the oral administration of the pharmaceutical composition.

In an embodiment said pharmaceutical formulation of complexed Celecoxib comprises Celecoxib, a copolymer of vinylpirrolidone and vinyl acetate, and sodium lauryl sulfate.

In an embodiment, said pharmaceutical formulation of complexed Celecoxib comprises
a. 5-40% by weight of Celecoxib, its salt, or derivatives thereof;
b. 40-80% by weight of a copolymer of vinylpyrrolidone and vinyl acetate; and
c. 1-30% by weight of sodium lauryl sulfate
wherein the particle size of said pharmaceutical formulation is less than 200 nm.

In an embodiment, said copolymer of vinylpyrrolidone and vinyl acetate is copovidone.

In an embodiment, vinylpyrrolidone and vinyl acetate ratio in said copolymer is VP:VA=60:40.

In an embodiment said crystalline Celecoxib is a micronized Celecoxib.

In an embodiment said micronized Celecoxib has a particle size in the range of 5-50 µm.

In an embodiment, said pharmaceutical formulation of complexed Celecoxib has an apparent solubility in water of at least 1 mg/mL.

In an embodiment, said pharmaceutical composition comprising a mixture of pharmaceutical formulation of complexed Celecoxib and crystalline, uncomplexed Celecoxib has biphasic dissolution profile: pharmaceutical formulation of complexed Celecoxib dissolves from the composition within less than 45 minutes, while crystalline Celecoxib dissolves continuously from the pharmaceutical composition.

In an embodiment, said complexed pharmaceutical formulation of Celecoxib dissolves from the composition within less than 30 minutes.

In an embodiment, said complexed pharmaceutical formulation of Celecoxib dissolves from the composition within less than 15 minutes.

In an embodiment, Celecoxib blood plasma level reaches 250 ng/mL therapeutic value in less than 60 minutes after the administration of said pharmaceutical composition comprising a mixture of pharmaceutical formulation of complexed Celecoxib and crystalline, uncomplexed Celecoxib.

In an embodiment, said blood plasma level is reached in less than 45 minutes.

In an embodiment, said blood plasma level is reached in less than 30 minutes.

In an embodiment, said blood plasma level is reached in less than 20 minutes.

In an embodiment, said blood plasma level is reached in less than 15 minutes.

In an embodiment, said pharmaceutical compositions comprising a mixture of pharmaceutical formulation of complexed Celecoxib and crystalline, uncomplexed Celecoxib provide faster onset of action for acute pain relief and lower GI related side effects compared to the currently available formulations.

In an embodiment, said complexes possess at least two of the properties described in a)-e).

In an embodiment, said complexes possess at least three of the properties described in a)-e).

In an embodiment, said pharmaceutical compositions comprise 50-200 mg Celecoxib that is complexed and 50-400 mg crystalline Celecoxib.

In an embodiment, said pharmaceutical compositions comprise 75-125 mg Celecoxib that is complexed Celecoxib and 75-125 mg crystalline Celecoxib.

In an embodiment, said pharmaceutical formulation of complexed Celecoxib is prepared by mixing 2-propanolic solution containing Celecoxib and copolymer of vinylpyrrolidone and vinyl acetate with an aqueous solution containing sodium lauryl sulfate.

In an embodiment, a pharmaceutical composition comprises said pharmaceutical formulation comprising a mixture of pharmaceutical formulation of complexed Celecoxib and crystalline Celecoxib together with a pharmaceutically acceptable carrier.

In an embodiment, said compositions further comprise additional pharmaceutical excipients.

In an embodiment, said pharmaceutical composition is suitable for oral, pulmonary, rectal, colonic, parenteral, intracistemal, intravaginal, intraperitoneal, ocular, otic, local, buccal, nasal, or topical administration.

In an embodiment, said compositions are suitable for oral administration.

In an embodiment, said pharmaceutical compositions are for use in the manufacture of a medicament for the treatment of osteoarthritis, rheumatoid arthritis, juvenile rheumatoid arthritis, ankylosing spondylitis, acute pain, primary dysmenorrhea.

In an embodiment, said pharmaceutical compositions are used for the treatment of osteoarthritis, rheumatoid arthritis, juvenile rheumatoid arthritis, ankylosing spondylitis, acute pain, primary dysmenorrhea.

In an embodiment, a method of treatment of osteoarthritis, rheumatoid arthritis, juvenile rheumatoid arthritis, ankylosing spondylitis, acute pain, primary dysmenorrhea comprises administration of a therapeutically effective amount of the pharmaceutical composition as described herein.

In an embodiment, a method for reducing the therapeutically effective dosage of Celecoxib compared to commercially available Celebrex® comprises oral administration of a pharmaceutical composition as described herein.

In an embodiment, the therapeutically effective Celecoxib blood plasma level (250 ng/mL) is reached within less than 60 minutes after the oral administration of said pharmaceutical formulation as described herein.

In an embodiment, said blood plasma level is reached in less than 45 minutes.

In an embodiment, said blood plasma level is reached in less than 30 minutes.

In an embodiment, said blood plasma level is reached in less than 20 minutes.

In an embodiment, said blood plasma level is reached in less than 15 minutes.

In an embodiment, food uptake has no effect on the early absorption of the compound and the time it takes to reach effective Celecoxib blood plasma level (250 ng/mL).

In an embodiment, said complexes show reduced fed/fasted effect compared to Celebrex®.

In an embodiment, said complexes have an onset of action of 12 minutes, which is faster than the existing formulations of Celecoxib.

In an embodiment the pharmaceutical compositions as described herein deliver early therapeutic blood plasma levels which is 250 ng/mL to ensure the fast pain relief and sustained Celecoxib dissolution to maintain the therapeutic blood plasma level for at least 12 h after the oral administration of the pharmaceutical composition.

In an embodiment, said pharmaceutical composition as described herein has biphasic dissolution profile: pharmaceutical formulation of complexed Celecoxib dissolves from the composition within 60 minutes, while crystalline Celecoxib has continuous dissolution.

In an embodiment, said complexed pharmaceutical formulation of Celecoxib dissolves from the composition within less than 45 minutes.

In an embodiment, said complexed pharmaceutical formulation of Celecoxib dissolves from the composition within less than 30 minutes.

In an embodiment, said complexed pharmaceutical formulation of Celecoxib dissolves from the composition within less than 20 minutes.

In an embodiment, said complexed pharmaceutical formulation of Celecoxib dissolves from the composition within less than 15 minutes.

In an embodiment, the pharmaceutical formulation of complexed Celecoxib is instantaneously redispersable in physiological relevant media.

In an embodiment, the pharmaceutical formulation of complexed Celecoxib has an apparent solubility in water of at least 1 mg/mL.

In an embodiment, the pharmaceutical formulation of complexed Celecoxib has a PAMPA permeability of at least $0.5 \times 10^{-6}$ cm/s when dispersed in FaSSIF or FeSSIF biorelevant media, which does not decrease in time at least for 3 months stored at 40° C.

In some embodiments, the pharmaceutical compositions may additionally include one or more pharmaceutically acceptable excipients, auxiliary materials, carriers, active agents or combinations thereof. In some embodiments, active agents may include agents useful for the treatment of any type of cancer.

The pharmaceutical composition as described herein can be formulated: (a) for administration selected from the group consisting of oral, pulmonary, rectal, colonic, parenteral, intracistemal, intravaginal, intraperitoneal, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

The compositions can be formulated by adding different types of pharmaceutically acceptable excipients for oral administration in solid, liquid, local (powders, ointments or drops), or topical administration, and the like.

In an embodiment, the dosage form is a solid dosage form.

Solid dosage forms for oral administration include, but are not limited to, capsules, tablets, pills, powders (sachet), orally disintegrating tablet, immediate release tablets and granules. In such solid dosage forms, the pharmaceutical composition of Celecoxib is admixed with at least one of the following: one or more inert excipients (or carriers): (a) fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide; (b) sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid; (c) binders, such as cellulose derivatives, acrylic acid derivatives, alginates, gelatin, polyvinylpyrrolidone, starch derivatives, dextrose, dextrates, dextrin, maltose, maltodextrin; (d) disintegrating agents, such as crospovidon, effervescent compositions, croscarmellose sodium and other cellulose derivatives, sodium starch glycolate and other starch derivatives, alginic acid, certain complex silicates and sodium carbonate; (e) solution retarders, such as acrylates, cellulose derivatives, paraffin; (f) absorption accelerators, such as quaternary ammonium compounds; (g) wetting agents, such as polysorbates, cetyl alcohol and glycerol monostearate; (h) lubricants such as talc, stearic acid and its derivatives, solid polyethylene glycols, sodium lauryl sulfate, glyceryl behenate, medium-chain triglycerides or mixtures thereof. For capsules, tablets, and pills, the dosage forms may also comprise buffering agents.

In an embodiment, the dosage form is a liquid dispersible granule, sachet, orally disintegrating tablet, chewing tablet, tablet for solution, tablet for suspension and immediate release tablet.

In an embodiment, said complexed Celecoxib and crystalline Celecoxib, and optionally said excipients, are blended together, granulated together, or combinations thereof.

In an embodiment, said dosage forms comprise the blended and/or granulated pharmaceutical formulation of complexed Celecoxib and crystalline Celecoxib together with pharmaceutically acceptable excipients selected from the group of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starches, microcrystalline cellulose, dicalcium phosphate, calcium carbonate, magnesium carbonate, magnesium oxide.

In an embodiment, said dosage forms comprise the blended and/or granulated pharmaceutical formulation of Celecoxib and crystalline Celecoxib with pharmaceutically acceptable excipients selected from the group of sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid.

Further disclosed herein is a liquid dispersible granule, sachet, orally disintegrating tablet, chewing tablet, tablet for solution, tablet for suspension and immediate release tablet comprising
 a. 5-95% pharmaceutical formulation of complexed Celecoxib;
 b. 5-95% crystalline Celecoxib;
 c. 5-95% fillers or extenders;
 d. 0.5-25% binders;
 e. 0.001-15% sweetening, flavoring, and perfuming agents;
 f. 5-95% disintegrants
wherein said liquid dispersible granule, sachet, orally disintegrating tablet, chewing tablet, tablet for solution, tablet for suspension and immediate release tablet disintegrates within 10 min in liquid.

In an embodiment, said disintegration time is between 0.1 min and 10 min.

In an embodiment, said disintegration time is between 0.1 min and 5 min.

In an embodiment, said disintegration time is between 0.1 min and 3 min.

In an embodiment, said disintegration time is between 0.1 min and 1 min.

In an embodiment, said liquid dispersible granules of complexed Celecoxib formulation are obtained by wet or dry processes.

In an embodiment, the Hausner-ratio of the said liquid dispersible granules of complexed Celecoxib formulations is less than 1.25.

In an embodiment, the Hausner-ratio of the said liquid dispersible granules of complexed Celecoxib formulations is between 1.00 and 1.11.

In an embodiment, the particle size (D(90)) of said liquid dispersible granules of complexed Celecoxib formulations is less than 2000 micrometers.

In an embodiment, 60-80% of the said liquid dispersible granules of complex celecoxib formulations are in the size range of 160-800 micrometers.

In an embodiment, said liquid is water, saliva, other physiologically or biologically acceptable fluid or liquid.

In an embodiment, the dosage form is a liquid dispersible granule, sachet, orally disintegrating tablet, chewing tablet, tablet for solution, tablet for suspension and immediate release tablet.

In an embodiment, said liquid dispersible granule, sachet, orally disintegrating tablet, chewing tablet, tablet for solution, tablet for suspension or immediate release tablet comprises the pharmaceutical formulation of complexed Celecoxib and crystalline Celecoxib together with pharmaceutically acceptable excipients selected from the group of fillers or extenders, such as, lactose, sucrose, glucose, mannitol, sorbitol, dextrose, dextrates, dextrin, erythritol, fructose, isomalt, lactitol, maltitol, maltose, maltodextrin, trehalose, xylitol, starch.

In an embodiment, said liquid dispersible granule, sachet, orally disintegrating tablet, chewing tablet, tablet for solution, tablet for suspension or immediate release tablet comprises the pharmaceutical formulation of complexed Celecoxib and crystalline Celecoxib together with pharmaceutically acceptable excipients selected from the group of sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid.

In an embodiment, said liquid dispersible granule, sachet, orally disintegrating tablet, chewing tablet, tablet for solution, tablet for suspension or immediate release tablet comprises the pharmaceutical formulation of complexed Celecoxib and crystalline Celecoxib together with pharmaceutically acceptable excipients selected from the group of disintegrants such as cross-linked polyvinylpyrrolidone, sodium-starch glycolate, croscarmellose-sodium, soy polysaccharides, colloidal silicon dioxide.

Further disclosed herein is liquid dispersible granule, sachet, orally disintegrating tablet, tablet, chewing tablet, tablet for solution, tablet for suspension and immediate release tablet comprising
 a. 5-95% stable pharmaceutical formulation of complexed Celecoxib;
 b. 5-95% crystalline Celecoxib;
 c. 0.5-95% fillers or extenders such as lactose, sucrose, glucose, mannitol, sorbitol, dextrose, dextrates, dextrin, erythritol, fructose, isomalt, lactitol, maltitol, maltose, maltodextrin, trehalose, xylitol, starch;
 d. 0.001-15% sweetening, flavoring, and perfuming agents such as saccharin, saccharin sodium, acesulfame potassium, alitame, aspartame, glycine, inulin, neohesperidin dihydrochalcone, neotame, sodium cyclamate, sucralose, tagatose, thaumatin, citric acid, adipic acid, fumaric acid, leucine, malic acid, menthol, propionic acid, tartaric acid;

e. 0.5-25% wetting agents, such as docusate sodium, sodium dodecyl sulfate, ammonium lauryl ether sulfate, benzalkonium chloride, benzethonium chloride, cetyl trimethylammonium bromide, polyoxyethelene alkylphenylethersm poloxamers, polyoxyethelene fatty acid glycerides, sorbitan esters;

f. 5-95% disintegrants such as cross-linked polyvinylpyrrolidone, sodium-starch glycolate, croscarmellose-sodium, soy polysaccharides, colloidal silicon dioxide;

wherein said liquid dispersible granule, sachet, orally disintegrating tablet, chewing tablet, tablet for solution, tablet for suspension and immediate release tablet disintegrates within 10 min.

In an embodiment, said disintegration time is between 0.1 min and 15 min.

In an embodiment, said disintegration time is between 0.1 min and 5 min.

In an embodiment, said disintegration time is between 0.1 min and 1 min.

In an embodiment, said liquid dispersible granules are obtained by wet or dry processes.

The pharmaceutical compositions of Celecoxib described herein show improvements related to (1) physical and chemical stability, (2) instantaneous redispersibility, (3) stability in colloid solution or dispersion in the therapeutic time window, (4) increased apparent solubility and permeability compared to the conventional Celecoxib formulation, (5) decreased time to onset of action for acute pain, (6) oral bioavailability, (7) decreased fed/fasted effect especially with respect to onset of action, and (8) good processability compared to Celebrex®.

In an embodiment, said compositions have good/instantaneous redispersibility of solid pharmaceutical compositions of Celecoxib in water and biologically relevant media, e.g.; physiological saline solution, pH=1.6 HCl solution, FessiF and FassiF media and gastro intestinal fluids, and adequate stability in colloid solutions and/or dispersion in the therapeutic time window.

In an embodiment, said compositions have increased apparent solubility and PAMPA permeability. In some embodiments, the apparent solubility and permeability of said compositions is at least 1 mg/mL and $0.5 \times 10^{-6}$ cm/s, respectively.

In another embodiment, the Celecoxib pharmaceutical compositions have an enhanced pharmacokinetic performance. The complex Celecoxib formulations show decreased time to onset of action when compared to the current oral formulation.

BRIEF DESCRIPTION OF THE DRAWINGS

The accompanying figures, which are incorporated and form part of the specification, merely illustrate certain embodiments and should not be construed as limiting the invention. They are meant to serve to explain specific modes to those skilled in the art.

EXAMPLES

Specific, non-limiting embodiments will further be demonstrated by the following examples.

Celecoxib Pharmaceutical Formulations

A solution mixture of complexed Celecoxib pharmaceutical formulation was prepared by mixing process. 2-propanolic solution (Solution 1) containing 10 mg/mL Celecoxib 40 mg/mL copovidone (copolymer of vinylpyrrolidone and vinyl acetate/Kollidon VA64) was mixed with aqueous solution (Solution 2) containing 20 mg/mL sodium lauryl sulfate. The solution mixture was produced at atmospheric pressure and ambient temperature. The flow rate ratio of the solutions (Solution 1 and Solution 2) were 40 mL/min and 20 mL/min, respectively.

A solution of complexed Celecoxib pharmaceutical formulation was prepared by dissolving 17.5 mg/mL Celecoxib, 70 mg/mL Copovidone (copolymer of vinylpyrrolidone and vinyl acetate/Kollidon VA64) and 4.375 mg/mL sodium lauryl sulfate in 2-propanol and water solvent mixture having volume ratio of 2:1. The dissolution process took place at atmospheric pressure and ambient temperature under stirring.

Both the solution mixture and solution of complexed Celecoxib pharmaceutical formulation was spray-dried (Yamato DL-410/GAS410). The production parameters used were $T_{inlet}$=95° C., drying airflow=0.8-0.85 m³/min, solution feed rate=6-20 mL/min, atomization pressure=1 bar, $T_{out}$=60-70° C. The spray-dried formulation was granulated and used for iv-vivo dog PK studies.

The prepared complexed Celecoxib pharmaceutical formulation comprised 5 to 40 weight % Celecoxib, 40 to 80 weight % copolymer of vinylpyrrolidone and vinyl acetate (copovidone) and 1 to 30 weight % sodium lauryl sulfate.

Liquid dispersible granules of the complexed Celecoxib pharmaceutical formulations were obtained by dry process. Compacts with uniform dimensions and mass were prepared of the solid Celecoxib pharmaceutical formulations. The compacts were broken up by physical impact in order to form granulates within appropriate mesh size. After that granulates were mixed with pharmaceutically acceptable excipients.

The solid, complexed Celecoxib pharmaceutical formulation was mixed with pharmaceutically acceptable excipients. After that compacts with uniform dimensions and mass were prepared from the powder mixtures comprising the pharmaceutical formulation of complexed Celecoxib. The compacts were broken up by physical impact in order to form granulates within appropriate mesh size.

Liquid dispersible granules were prepared by compacting 400-3000 mg solid complexed Celecoxib pharmaceutical formulation comprising copolymer of vinylpirrolidone and vinyl acetate and sodium lauryl sulfate using a flat faced tooling with 4-23 mm diameter and pressed with 0.1-4.5 ton load. The compacts were broken up by physical impact to form granules. The particle size of the granulates was controlled by sieving with appropriate mesh size to achieve 160-800 micrometers particle size.

Celecoxib Pharmaceutical Compositions

The liquid dispersible granules containing the pharmaceutical composition of Celecoxib were prepared by blending the granules of the complexed Celecoxib formulation and the unprocessed or granulated micronized Celecoxib. Micronized Celecoxib granules were prepared by compacting 1 g micronized Celecoxib using a flat faced tooling with 15.8 mm diameter and pressed with 1.5 ton load. The compacts were broken up by physical impact to form granules with max. 800 micrometers particle size. The pharmaceutical compositions comprised 50-200 mg Celecoxib equivalent from the complexed Celecoxib pharmaceutical formulation and 50-400 mg crystalline Celecoxib. The particle size of the unprocessed, micronized Celecoxib was between 0.5-50 micron.

Improved Apparent Solubility of Celecoxib Pharmaceutical Compositions

The apparent solubility of the complexed Celecoxib pharmaceutical formulation, crystalline Celecoxib (micronized), granulated micronized Celecoxib and Celecoxib pharmaceutical composition was measured by UV-VIS spectroscopy at 251 nm at room temperature. A blend comprising 10 mg Celecoxib equivalent of complexed Celecoxib pharmaceutical formulation and 20 mg granulated micronized Celecoxib was prepared. The samples were dispersed in ultrapurified in 1-50 mg/mL Celecoxib equivalent concentration range. The resulting solutions were filtered by 100 nm disposable syringe filter. The Celecoxib content in the filtrate was measured by UV-Vis spectrophotometry and the apparent solubility was calculated. The filtrate may contain Celecoxib particles which could not be filtrated out using 100 nm pore size filter.

The apparent solubility of the complexed Celecoxib pharmaceutical formulation was at least 34 mg/mL, when 50 mg/mL Celecoxib equivalent formulation was dispersed in ultrapurified water, respectively.

The apparent solubility of crystalline Celecoxib (micronized) was 2.85 µg/mL when it was redispersed at 2 mg/mL concentration in ultrapurified water.

The apparent solubility of granulated Celecoxib (micronized) was 0.47 µg/mL when it was redispersed at 2 mg/mL concentration in ultrapurified water.

The apparent solubility of Celecoxib pharmaceutical composition was at least 5.98 mg/mL when it was redispersed at 20 mg/mL Celecoxib equivalent concentration in ultrapurified water.

Improved Dissolution Profile of Celecoxib Pharmaceutical Composition

Figure 1:
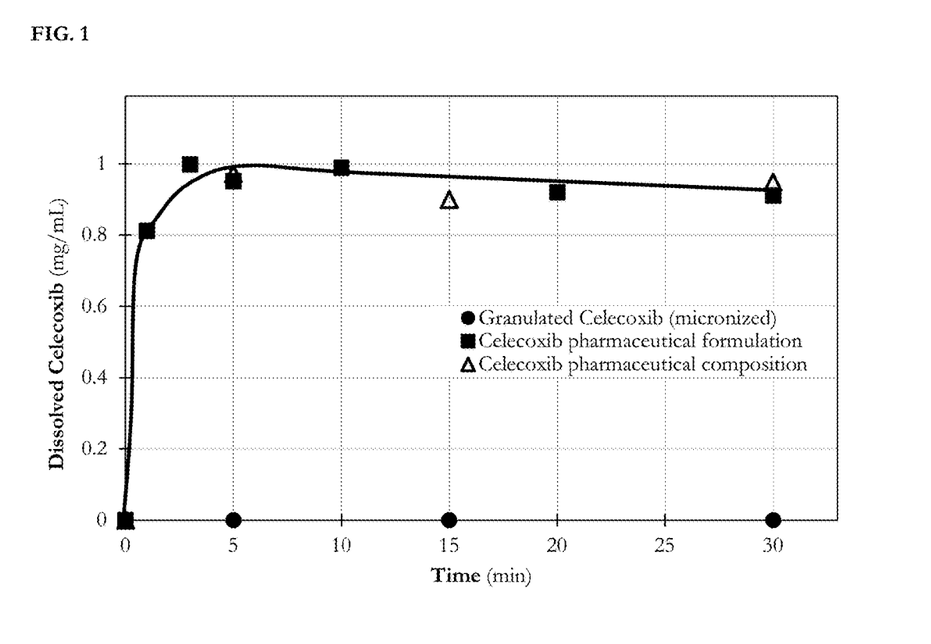
FIG. 1 shows the dissolution profile of Celecoxib pharmaceutical composition, complexed Celecoxib pharmaceutical formulation and crystalline Celecoxib (micronized).
Figure 2:
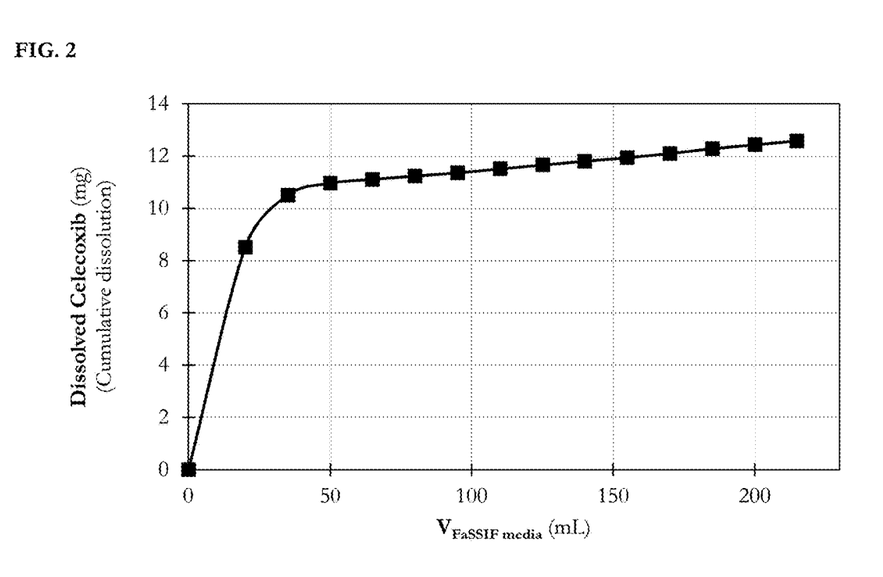
FIG. 2 shows the cumulative dissolution of Celecoxib pharmaceutical composition.
Figure 3:
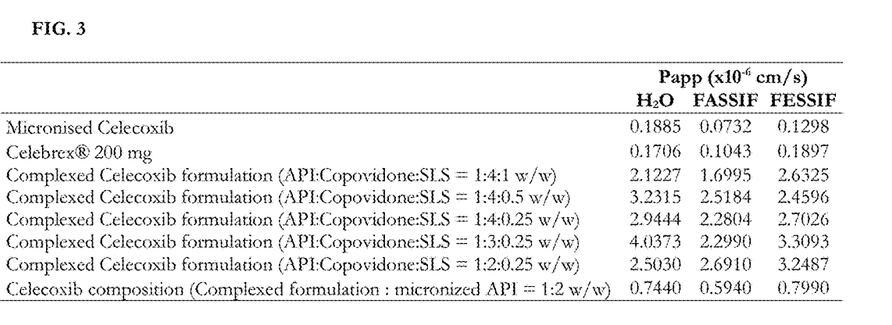
FIG. 3 shows the PAMPA permeability of different Celecoxib compositions: micronized Celecoxib, Celebrex, complexed Celecoxib formulations and Celecoxib pharmaceutical formulation.

Comparative dissolution tests were performed by dispersing the Celecoxib pharmaceutical composition, complexed Celecoxib pharmaceutical formulation and granulated Celecoxib (micronized) in ultrapure water. (FIG. 3). The blend of the investigated pharmaceutical composition comprised 10 mg Celecoxib that is complexed and 20 mg granulated micronized Celecoxib. The investigated concentration of Celecoxib was 1 mg/mL for the complexed pharmaceutical formulation and 2 mg/mL for granulate Celecoxib (micronized) in each cases alone or combination.

Figure 4:
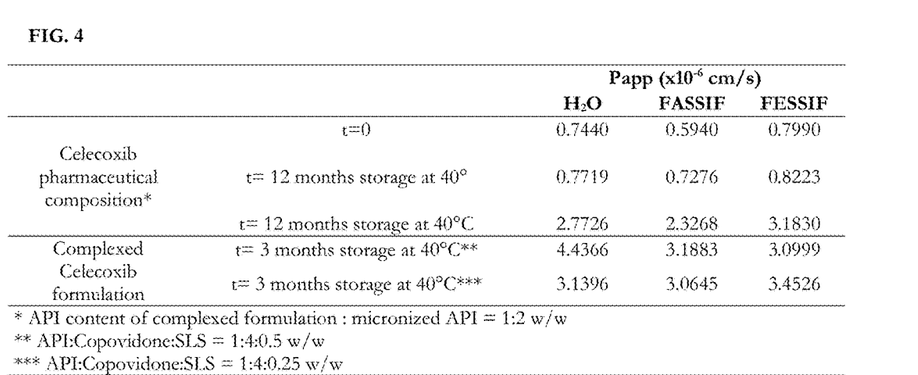
FIG. 4 shows the PAMPA permeability of Celecoxib pharmaceutical composition at t=0 and t=12 months when stored at 40° C. and complexed Celecoxib formulation stored at 40° C. at t=3 months

Cumulative drug dissolution test was performed on the pharmaceutical composition (FIG. 4). The blend of the investigated pharmaceutical composition comprised 10 mg Celecoxib equivalent of the complexed Celecoxib pharmaceutical formulation and 20 mg granulated micronized Celecoxib. The dissolution medium was FaSSIF biorelevant media containing 2 mg/mL Kollidon VA64 and 0.5 mg/mL sodium lauryl sulfate. At the beginning 30 mg blend was dissolved in 20 mL dissolution medium and shaken for 3 minutes with 300 rpm. After shaking, it was centrifuged with 3600 rpm for 1 minute. After centrifuging, 15 mL fluid was taken out from the top. The resulting solution was filtered by 100 nm disposable syringe filter. The Celecoxib content in the filtrate was measured by RP-HPLC measurement and the dissolved Celecoxib concentration was calculated. The filtrate may contain Celecoxib particles which could not be filtrated out using 100 nm pore size filter. The dissolution medium was replaced with 15 mL fresh FaSSIF to maintain the sink condition. The released drug quantity was determined every 4 minutes be repeating the above steps.

Comparative in-Vitro PAMPA Assays

PAMPA permeability of Celecoxib pharmaceutical composition, complexed Celecoxib pharmaceutical formulation, crystalline Celecoxib (micronized) and Celebrex® was measured and compared. PAMPA permeability measurements were performed as described by M. Kansi et al. (Journal of medicinal chemistry, 41, (1998) pp 1007) with modifications based on S. Bendels et al (Pharmaceutical research, 23 (2006) pp 2525). Permeability was measured in a 96-well plate assay across an artificial membrane composed of dodecane with 20% soy lecithin supported by a PVDF membrane (Millipore, USA). The receiver compartment was phosphate buffered saline (pH 7.0) supplemented with 1% sodium dodecyl sulfate. The assay was performed at room temperature; incubation time was 4 hours in ultrapurified water or 10-20 and 30 minutes in simulated saliva, respectively. The concentration in the receiver compartment was determined by UV-VIS spectrophotometry (Thermo Scientific Genesys S10). The Celecoxib concentration in the donor compartment was 0.25-3 mg/mL for the pharmaceutical composition and 0.25-2 mg/mL in all other cases. The blend of the pharmaceutical compositions comprised 10 mg Celecoxib equivalent of the complexed Celecoxib pharmaceutical formulation and 20 mg granulated micronized Celecoxib.

The PAMPA permeability of the Celecoxib pharmaceutical compositions was above 0.5×10-6 cm/s when redispersed in water, FaSSIF and FeSSIF, while it was below 0.2×10-6 cm/s for the Celebrex. PAMPA permeability of the Celecoxib pharmaceutical formulation in water, FaSSIF and FeSSIF media was above $1.5 \times 10^{-6}$ cm/s. PAMPA permeability of crystalline Celecoxib (micronized) in water, FaSSIF and FeSSIF media was below $0.2 \times 10^{-6}$ cm/s (FIG. 3).

Stability of the Celecoxib Solid Pharmaceutical Composition

PAMPA permeabilities of the Celecoxib pharmaceutical composition were used to monitor the physical stability of the pharmaceutical composition. PAMPA permeability was measured after storage at different conditions. 3 months storage at 40° C. showed no significant decrease in the measured PAMPA permeability under any of the conditions tested (FIG. 4).

In-Vivo Pharmacokinetics

In-Vivo PK Test in Large Animals

Figure 5:
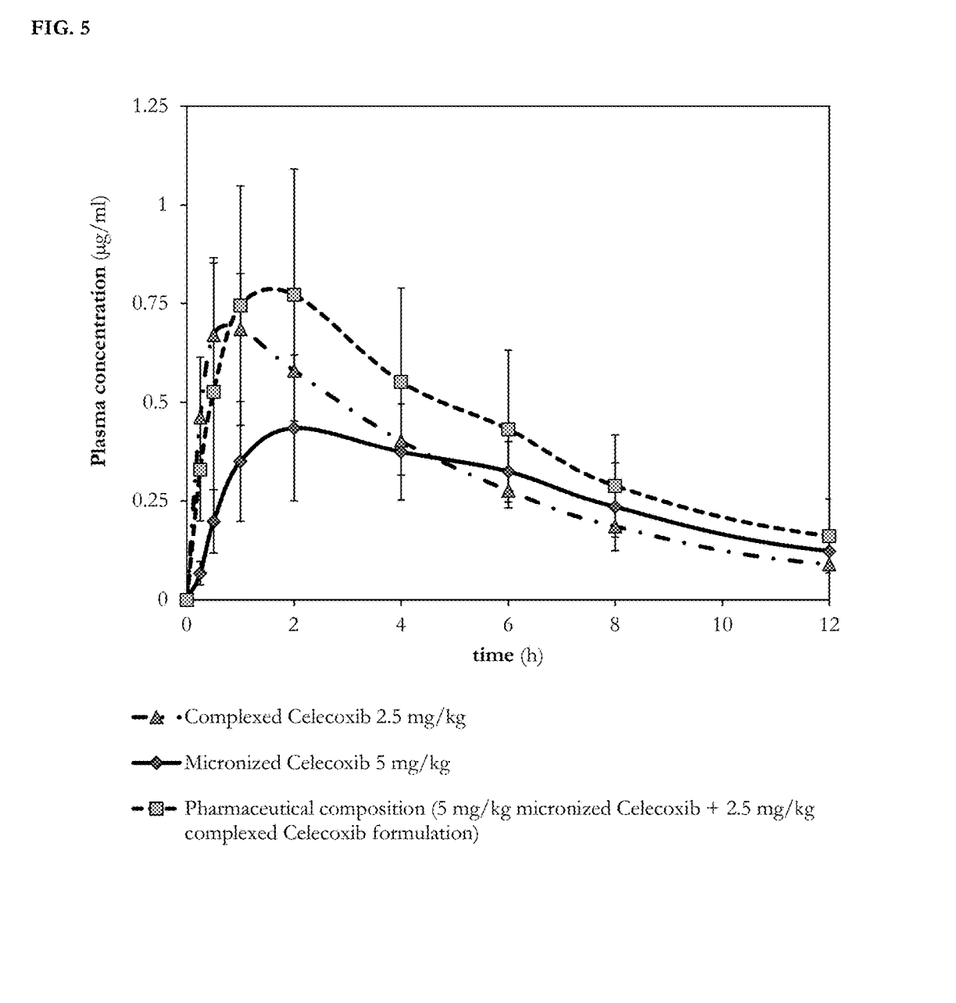
FIG. 5 shows the plasma concentrations of celecoxib following the administration of the following test items orally as dispersed granulates: complexed pharmaceutical formulation (2.5 mg/kg), micronized Celecoxib (5 mg/kg), pharmaceutical composition as described herein (2.5 mg pharmaceutical formulation and 5 mg/kg crystalline micronized celecoxib) to beagle dogs following a high-fat meal (N=4).

A beagle dog study using the granulated complexed pharmaceutical formulation, micronized Celecoxib and the pharmaceutical composition was performed. The test items were administered orally as dispersed granulates (complexed pharmaceutical formulation (2.5 mg/kg), micronized Celecoxib (5 mg/kg), pharmaceutical composition (2.5 mg complexed pharmaceutical formulation+5 mg/kg micronized Celecoxib) to beagle dogs following a high-fat meal. The absorption of Celecoxib from the pharmaceutical formulation was rapid with $t_{250\ ng/ml}$ at 12 minutes and $t_{max}$ at 45 minutes. The absorption of the Celecoxib was slow for the micronized compound reaching $t_{250\ ng/ml}$ at 45 minutes and $t_{max}$ at 2 hours, however, at late time points plasma concentrations exceeded the plasma concentration observed for the pharmaceutical formulation. The pharmaceutical composition delivered both rapid early absorption with $t_{250\ ng/ml}$ at 12 minutes and higher later time point plasma concentrations when compared to the pharmaceutical formulation or with micronized celecoxib (FIG. 5).

From the foregoing description, one skilled in the art can easily ascertain the essential characteristics of this invention, and without departing from the spirit and scope thereof, can make various changes and modifications to adapt it to various usages and conditions.

What is claimed is:

1. A pharmaceutical composition comprising
   i. pharmaceutical formulation of complexed Celecoxib comprising
      a) 5-40 weight % Celecoxib;
      b) 40-80 weight % copolymer of vinylpyrrolidone and vinyl acetate; and
      c) 5-30 weight % sodium lauryl sulfate;
   ii. crystalline Celecoxib; and
   iii. optionally pharmaceutically acceptable excipient;
wherein said pharmaceutical composition characterized in that it possesses at least one of the following properties:
   a) is instantaneously redispersable in physiological relevant media;
   b) has an apparent solubility in water of at least 1 mg/mL;
   c) has biphasic dissolution profile: pharmaceutical formulation of Celecoxib dissolves from the composition within 45 minutes, while crystalline Celecoxib has continuous dissolution;
   d) has a PAMPA permeability of at least $0.5 \times 10^{-6}$ cm/s when dispersed in FaSSIF or FeSSIF biorelevant media, which does not decrease in time at least for 3 months stored at 40° C.; and
   e) has a blood plasma level that reaches 250 ng/ml Celecoxib within 60 minutes when administered orally.

2. The pharmaceutical composition as recited in claim 1, wherein said crystalline Celecoxib is micronized Celecoxib.

3. The pharmaceutical composition as recited in claim 2, wherein the main particle size of said micronized Celecoxib is in range of 3-10 μm.

4. The pharmaceutical composition as recited in claim 1, wherein said pharmaceutical composition shows earlier time to onset of action when compared to the commercially available Celecoxib preparation Celebrex®.

5. The pharmaceutical composition as recited in claim 1, wherein said pharmaceutical composition possesses at least two of the properties described in a-e.

6. The pharmaceutical composition as recited in claim 1, wherein said pharmaceutical composition possesses at least three of the properties described in a-e.

7. The pharmaceutical composition comprising the complexed pharmaceutical formulation of Celecoxib and crystalline Celecoxib according to claim 1 together with a pharmaceutically acceptable carrier.

8. The pharmaceutical composition comprising the complexed pharmaceutical formulation of Celecoxib and crystalline Celecoxib according to claim 1, wherein said pharmaceutical composition is suitable for oral administration.

9. The pharmaceutical composition according to claim 8, wherein said pharmaceutical composition is suitable for the preparation of liquid dispersible granule, sachet, orally disintegrating tablet, chewing tablet, tablet for solution, tablet for suspension and immediate release tablet dosage forms.

10. The pharmaceutical composition according to claim 9, wherein said pharmaceutical composition comprises liquid dispersible granules of the complexed pharmaceutical formulation of Celecoxib and crystalline Celecoxib according to claim 1.

11. A method of treatment of osteoarthritis, rheumatoid arthritis, juvenile rheumatoid arthritis, ankylosing spondylitis, acute pain, primary dysmenorrhea comprising administration of a therapeutically effective amount of the pharmaceutical composition according to claim 1.

12. A method for reducing $t_{max}$ and time to onset of action when compared to the commercially available Celecoxib preparation Celebrex®, said method comprising oral administration of a pharmaceutical composition according to claim 7.

13. The pharmaceutical composition as recited in claim 1, wherein plasma concentration of Celecoxib greater than 250 ng/ml is achieved within 60 minutes.

14. The pharmaceutical composition of claim 13, wherein said plasma concentration is maintained for at least 12 hours.

* * * * *